United States Patent
Kadokami et al.

[11] Patent Number: 6,090,256
[45] Date of Patent: Jul. 18, 2000

[54] APPARATUS FOR ELECTROPHORESIS

[75] Inventors: Yoichi Kadokami, Hokkaido; Bunsei Kawakami; Yoshihisa Kawamura, both of Tsuruga, all of Japan

[73] Assignee: Toyo Boseki Kabushiki Kaisha, Osaka, Japan

[21] Appl. No.: 09/058,442

[22] Filed: Apr. 9, 1998

[30] Foreign Application Priority Data

Apr. 11, 1997 [JP] Japan .................................. 9-093997
Apr. 14, 1997 [JP] Japan .................................. 9-096195
Apr. 17, 1997 [JP] Japan .................................. 9-100171

[51] Int. Cl.$^7$ .................................................. G01N 27/26
[52] U.S. Cl. ........................................... 204/616; 204/606
[58] Field of Search .................................. 204/600, 606, 204/618, 621, 456, 466

[56] References Cited

U.S. PATENT DOCUMENTS 5,888,364  3/1999  Schuette ................................. 204/466

*Primary Examiner*—Jill Warden
*Assistant Examiner*—Alex Noguerola
*Attorney, Agent, or Firm*—Leydig, Voit & Mayer, Ltd.

[57] ABSTRACT

An electrophoresis apparatus comprising an arched lid 2 covering an electrophoresis tank 1, a suction opening 4 set in one end of the lid 2 and an exhaust opening 7 set in the other end of the lid 2. On the outside of the suction opening 4 is set a fan 5. The fan 5 absorbs the outside air, which flows along the inner side of the lid 2 and is exhausted from the exhaust opening 7 together with the vapor generated during electrophoresis, thereby preventing clouding and bedewing of the inner surface of the lid. Consequently, the inside of the electrophoresis tank 1 can be safely observed without opening the transparent or semi-transparent lid 2 but through it.

19 Claims, 16 Drawing Sheets

APPARATUS FOR ELECTROPHORESIS

FIELD OF THE INVENTION

The present invention relates to an apparatus for electrophoresis. More particularly, the present invention relates to an apparatus for electrophoresis having improved operability, safety and control functions.

BACKGROUND OF THE INVENTION

An electrophoresis is a general analytical technique widely used in various industrial fields for fundamental researches and various examinations in biochemistry. Among many of such apparatuses, a horizontal submarine electrophoresis apparatus has been used for the analysis of nucleic acids. This horizontal submarine electrophoresis apparatus comprises a simple structure comprising a cathode and an anode set on the bottom of a box type electrophoresis tank, and a power supply. In addition, a transparent lid for safety purposes is generally set on the top part of the electrophoresis tank.

Such electrophoresis apparatus is conventionally associated with inevitable occurrence of water vapor during electrophoresis due to a temperature elevation of a buffer, and the lid becomes cloudy and bedewed, making the observation of the inside of the electrophoresis tank extremely difficult. For example, under an ordinary temperature, the inside becomes completely invisible within 5 minutes after initiation of the electrophoresis.

When the lid is opened, moreover, a power supply part may become wet due to water droplets from the lid, possibly creating a dangerous situation. In addition, there have been safety and structural problems, since the operator may use the device with the lid open for easy operation during use. Inasmuch as the lid is of the similar size with the electrophoresis tank, a space should be secured to temporarily place the lid once it is removed. The electrophoresis tank is inevitably placed on the operator's side of the working table for the convenient addition of samples, and the power supply therefore is set in the rear part of the working table, which is on the distal end from the operator. Thus, the power cords connecting the both and the lid are placed in between the electrophoresis tank and power supply, and when the lid carries water, it could wet the power supply. Particularly when plural electrophoresis apparatuses are used simultaneously, a wide space on the working table is occupied and the power supply may become wet due to water droplets from the lid, thereby increasing the risk of electric leakage and electrification.

On the other hand, various attempts have been heretofore made to prevent electrification upon lid opening during operation. For example, a power cord may be connected to a lid which, once opened, cuts conductivity from the power supply. Alternatively, a power cord may be set only when the lid is shut, and the lid may not open unless the power cord is removed. These methods, nevertheless, degrade the operability of the apparatus to a greater degree.

While the size of the electrophoresis tank to be employed according to the object varies, a lower service voltage or a greater distance between the cathode and anode produces better resolution. The resolution is generally expressed by the following relational formula:

Resolution ($\phi$)=$\kappa$V (voltage)/D (distance between electrodes) (V/cm)

wherein $\kappa$ is a constant which is determined by the concentration of agarose gel, kind of buffer, temperature and the like.

The distance between the cathode and anode is practically determined according to the size of the electrophoresis tank, and the service voltage is determined in relation to the migration time. The resolution ($\phi$) is in inverse proportion to the migration time. The electrophoresis is practically carried out to achieve a certain range of resolution, and the resolution is controlled by the service voltage.

The electrophoresis apparatus for a minigel is widely used for its rapid performance rather than the resolution. For the assays of DNA and determinations of reactions, a long migration distance is not necessary, nor is the resolution required. Thus, an electrophoresis apparatus for minigel mostly suffices for general use.

However, an accurate determination of the molecular weight by electrophoresis requires a certain distance between electrodes, thus necessitating a large electrophoresis tank. The use of such large electrophoresis tank instead of an electrophoresis apparatus for minigel is disadvantageous in that the long distance between electrodes requires high voltage, while a power supply therefor is difficult to secure and even more dangerous. Therefore, at least two kinds of large and small electrophoresis tanks have been needed for routine analysis.

It is therefore an object of the present invention to provide a safe electrophoresis apparatus generally used in wide applications, such as a horizontal submarine electrophoresis apparatus, wherein the lid of a migration tank does not suffer from clouding or bedewing due to the water vapor generated during electrophoresis, thus permitting an easy observation of the inside of the electrophoresis tank without opening the lid, but through it.

Another object of the present invention is to develop an electrophoresis apparatus capable of both an accurate electrophoresis and a rapid electrophoresis using a minigel.

SUMMARY OF THE INVENTION

According to the present invention, it has now been found that, by forming an air suction opening and an exhaust opening in an electrophoresis apparatus, thereby flowing the air in the space between the electrophoresis tank and the lid, particularly constantly exposing the inner surface of the lid (the plane of the lid opposite to the bottom of the electrophoresis tank when the lid is placed on the electrophoresis tank) to the flowing air, the water vapor occurred can be efficiently removed and the clouding and bedewing of the lid can be completely prevented.

Thus, the present invention provides an electrophoresis apparatus comprising an electrophoresis tank and a transparent or semi-transparent lid, said apparatus possessing a means for forcibly discharging the air in the space between said electrophoresis tank and said lid to the outside or a means for forcibly absorbing the outside air into said space, an air suction opening and an air exhaust opening, preferably an air suction opening in the periphery of the lid, and an air exhaust opening in the periphery opposing said suction opening.

It has also been found that a hinge set on the lid saves the space necessary for temporarily placing the lid when it is not in use, and prevents the power supply and its surrounding area from getting wet with water, since the water droplets from the opened lid-drop in the same direction. Moreover, the open and shut movement of the lid can be a device to open and shut electrode terminals, thus improving operability and safety of the apparatus. Accordingly, the present invention provides, of the above-mentioned electrophoresis apparatuses, one having a lid that opens and shuts on the hinge having a fulcrum on one side or a pair of opposing sides of the electrophoresis tank. The present invention moreover provides the above-mentioned electrophoresis apparatus wherein the contact between the electrode terminal connected to an electrode set inside the electrophoresis tank, and the power supply applying a D.C. voltage on the electrode is controlled by the open and shut of the lid.

It has been moreover found that a detachable electrode can freely set the distance between the electrodes. Accordingly, the present invention provides the above-mentioned electrophoresis apparatus comprising cathode and anode electrodes detachably formed in the electrophoresis tank. The present invention also provides the above-mentioned electrophoresis apparatus comprising electrode racks respectively equipped with a cathode connected to a cathode terminal and an anode connected to an anode terminal detachably set within the electrophoresis tank.

DETAILED DESCRIPTION OF THE INVENTION

Figure 1A:
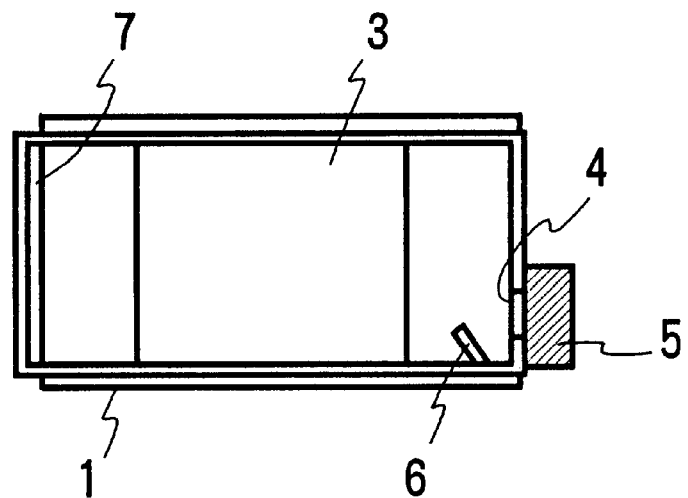
FIGS. 1(a)–(d) show one embodiment of the inventive electrophoresis apparatus, wherein (a) is a top view, (b) is a side view, (c) is a cross sectional view of the portion in (b) which is enclosed with a broken line, and (d) is a schematic showing of the air flow in the electrophoresis tank.
Figure 1B:
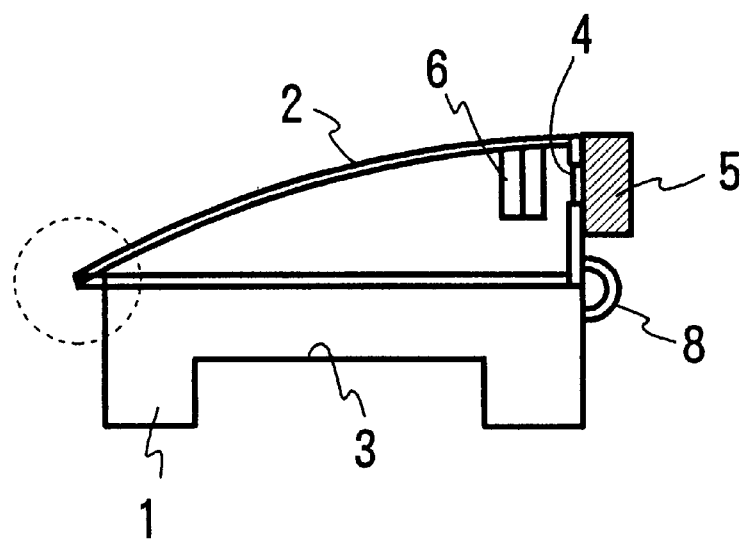
Figure 1C:
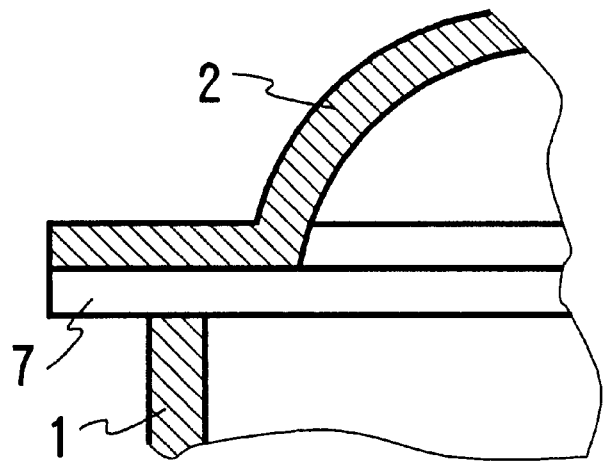

The electrophoresis tank to be used in the present invention suffers from generation of water vapor due to the increase in the temperature of a buffer during electrophoresis, and is typically exemplified by horizontal submarine electrophoresis tank. The horizontal submarine electrophoresis tank has a convex platform to maintain a migration carrier such as an agarose gel and a polyacrylamide gel. A rectangular parallelepiped box may be used as a substitute therefor as mentioned later.

While the material of the electrophoresis tank is subject to no particular limitation as long as it is non-conductive, the use of a heat resistant material advantageously permits washing and sterilization using warm water (60–70° C.) or hot water (ca. 100° C.), or autoclaving (2 atm, 120° C.) for inactivation of the enzyme attached. The material having superior heat resistance may be, for example, heat resistant plastic such as polyethylene terephthalate, polypropylene, polycarbonate and the like.

The lid may be any as long as it is not opaque, so that the inside of the electrophoresis tank can be visually observed when the lid is placed on the electrophoresis tank. Thus, a colored or colorless, transparent or semi-transparent lid is sufficient for this purpose. The shape of the lid is not subject to any limitation and may be flat or square, as long as it can cover the opening of the electrophoresis tank and tightly seal the electrophoresis tank except for the suction opening and exhaust opening. In addition, the material of the lid is free of any limitation, and transparent plastic is generally used.

The air suction opening and exhaust opening may be formed either on the electrophoresis tank or the lid. For an efficient exposure of the inner surface of the lid to the flowing air, an air suction opening is preferably formed in the periphery of the lid, and an air exhaust opening is preferably formed in the periphery facing said suction opening.

The inventive electrophoresis apparatus has at least either a means for forcibly discharging the air in the space between the electrophoresis tank and the lid to the outside (hereinafter to be referred to as discharge means) or a means for forcibly absorbing the outside air into said space (hereinafter to be referred to as suction means). These discharge means and suction means can be realized by a fan or a pump permanently or temporarily installed on the inside or outside of the exhaust opening and suction opening.

While the material of the electrode rack is free of limitation as long as it is non-conductive, the above-mentioned heat resistant material is preferably used.

The hinge includes various types made from various materials. Any kind thereof can be used as long as it has sufficient strength.

In another embodiment of the electrophoresis apparatus of the present invention, the conductivity can be controlled by the open/shut of the lid, wherein electrode terminals connected to the cathode and anode, such as a platinum electrode installed in the electrophoresis tank, come into contact with other terminals connected to the lid, only when the lid is shut. On the other hand, the terminals of the lid are connected to a D.C. power supply via a power cord. Thus, when the lid is open, the terminals of the electrophoresis tank and the lid are respectively disconnected mechanically, thereby making the electrophoresis tank non-conductive. The structure of the terminal may be any as long as it can provide a conductive contact, and may have any shape.

According to the electrophoresis apparatus of the present invention, the outside air is forcibly absorbed from the suction opening and forcibly discharged from the exhaust opening together with the water vapor generated in the space, using a discharge means and a suction means formed in the electrophoresis apparatus. Thus, occurrence of clouding and bedewing of the inner surface of the lid can be prevented, which in turn makes it possible to safely observe the inside of the electrophoresis tank without opening the transparent or semi-transparent lid but through it.

The clouding and bedewing of the inner surface of the lid can be efficiently prevented by forming an air suction opening in the periphery of the lid and an air exhaust opening in the periphery facing said suction opening, so that the flowing air can efficiently come into contact with the inner surface of the lid.

According to the electrophoresis apparatus of another embodiment of the present invention, it has a lid that opens and shuts with the aid of a hinge. Therefore, the operability can be improved, and the vapor bedewed during the electrophoresis can be prevented from leaking outside the electrophoresis tank by modifying the lid structure or by changing the position of the hinge, thereby minimizing the surrounding area that may become wet. In the conventional electrophoresis apparatus, the lid occupies the same amount of space as does the electrophoresis tank for temporary storage when the lid is not used. According to another electrophoresis apparatus of the present invention, in contrast, the lid is opened and maintained in that state, requiring no additional space on the test table. In addition, the open and shut action of the lid simultaneously provides a safety means for a power supply, because the conductivity or otherwise can be secured by the open and shut action of the lid.

In another embodiment of the present invention, since mutually separate cathode and anode electrodes are detachably set in an electrophoresis tank, or electrode racks equipped with a cathode connected to a cathode terminal and an anode connected to an anode terminal are detachably set in an electrophoresis tank, the distance between the two electrodes can be freely changed. This in turn enables not only the control of the resolution and migration speed under the same voltage, but also the use of large-sized electrophoresis tanks for electrophoresis using a minigel.

A conventional electrophoresis apparatus comprises cathode and anode electrodes directly fixed on the bottom of the electrophoresis tank. Thus, a step of directly fixing the electrodes is necessary for the manufacture, and washing of the inside of the electrophoresis tank after use requires high attention not to damage the exposed electrodes. In the electrophoresis apparatus of the present invention, in contrast, the cathode and anode electrodes or the both electrode racks can be detached from the electrophoresis tank. This makes washing of the entire electrophoresis tank after use quite easy, and the possibility of damaging the electrodes is obliterated. In addition, since the electrode directly attached to the inside of the conventional electrophoresis tank can be detachably attached to an electrode rack, the electrode can be easily set and the production efficiency can be increased.

The embodiment of the present invention is explained in the following by referring to the Figures. FIG. 1 shows one embodiment of the electrophoresis apparatus of the present invention, wherein a lid 2 having an arched inner surface is set on the electrophoresis tank 1. On the bottom of the electrophoresis tank 1 is formed a convex platform 3, and the cathode and anode (not shown) are formed on the both ends thereof in the migration direction. The top part of the lid 2 covering the electrophoresis tank 1 is on one end thereof in the migration direction (right end in FIG. 1) and the lid has increasing gradients toward the other end in the migration direction. The entire lid is composed of transparent plastic.

A hinge 8 connects the electrophoresis tank 1 and lid 2, and by lifting the left end of the lid 2 toward right, the lid can be opened Then, an agarose gel can be retained on the platform 3 in the electrophoresis tank 1.

To be specific, the opening of the electrophoresis tank is square and the outer periphery of the lid is also a square corresponding to the opening of the electrophoresis tank. The top surface of the lid slides down from the center axis used when the lid is opened with the aid of hinge 8, toward the opposite end of the lid. The sliding surface is arched, such that the gradient becomes greater toward the downward direction of the lid.

A circular suction opening 4 is perforated on the side near the top of the lid 2. The position thereof is in the upper part of said side and toward a corner from the center in the direction forming a right angle with the direction of migration. On the outside of the suction opening 4 is attached a fan 5 as a suction means. In addition, a transparent plastic baffle plate 6 has been attached to the inside of the suction opening 4, forming an angle θ with the direction of migration.

Figure 1D:
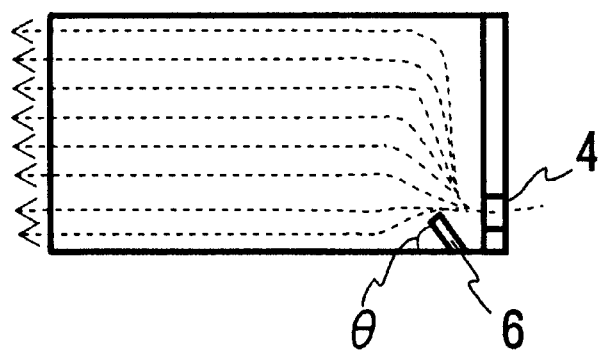

In FIG. 1(d), the direction of the air sent from a fan 5 via the suction opening 4 is the same with the migration direction, and the wind from the fan 5 hits the baffle plate 6 at an angle θ. By setting the suction opening 4 at a biased position and attaching the baffle plate 6, the air can be efficiently moved along the entirety of the inner surface of the lid 2 by a single fan 5. While the angle θ varies according to the shape and size of the electrophoresis tank 1 and the lid 2, it is generally about 30–50°, preferably 35–45°.

The vapor generated in the electrophoresis tank 1 can be efficiently discharged to the outside from the discharge opening slit 7 which is the entirety of the other end of the lid 2 in the migration direction (left end in FIG. 1). Therefore, by forming an air exhaust opening 7 in the periphery opposing the air suction opening 4 formed in the periphery of the lid 2, as shown in FIG. 1(d), the flowing air can be efficiently brought into contact with the inner surface of the lid 2, whereby occurrence of clouding and bedewing can be effectively prevented.

Figure 2:
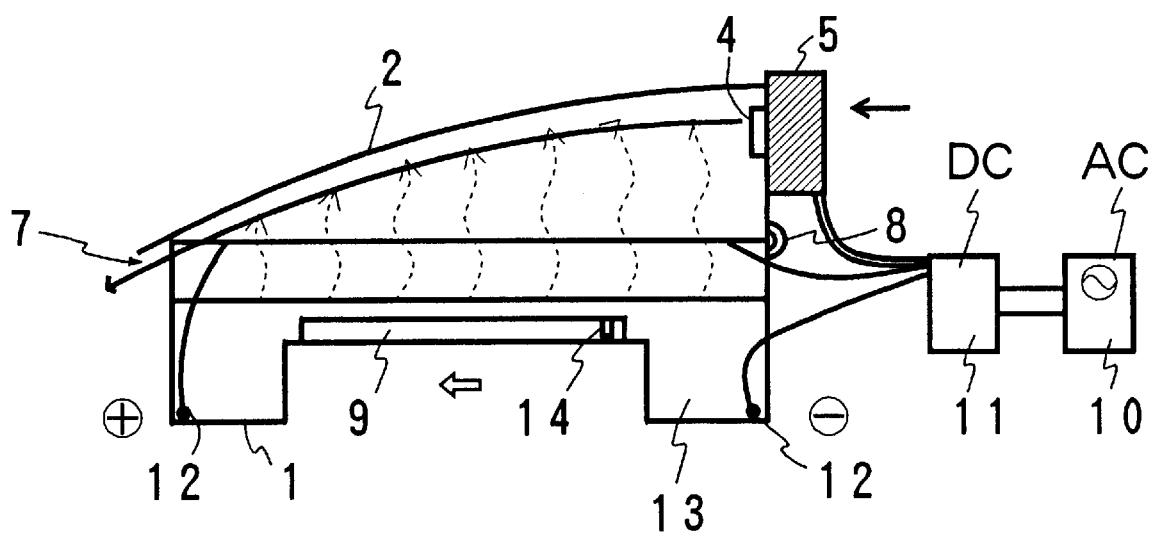
FIG. 2 is a structural view showing the operation of the electrophoresis apparatus shown in FIG. 1.

FIG. 2 shows the electrophoresis apparatus shown in FIG. 1 during electrophoresis, wherein the broken line denotes the movement of vapor and the solid line arrow shows the flow of the air.

The direct current obtained from a commercial AC. power supply 10 via a D.C. power supply 11 forms an electric field in a buffer 13 by the platinum cathode and platinum anode electrodes 12. A sample is placed in a slot 14 of gel 9 placed in this electric field. The sample moves in the direction of the electric field afterward direction in FIG. 2). Along therewith, the air is absorbed from the outside by the fan 5, flows along the inner surface of the lid 2 from the suction opening 4, and is discharged from the exhaust opening 7 together with the water vapor generated from the buffer 13.

Figure 3A:
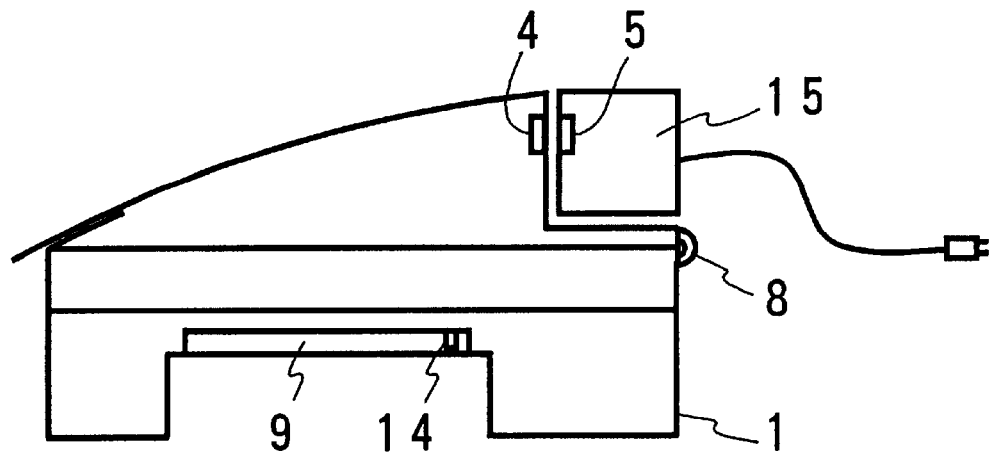
FIGS. 3(a), (b) are structural views showing another embodiment of the electrophoresis apparatus of the present invention, wherein (a) is a top view and (b) is a side view.
Figure 3B:
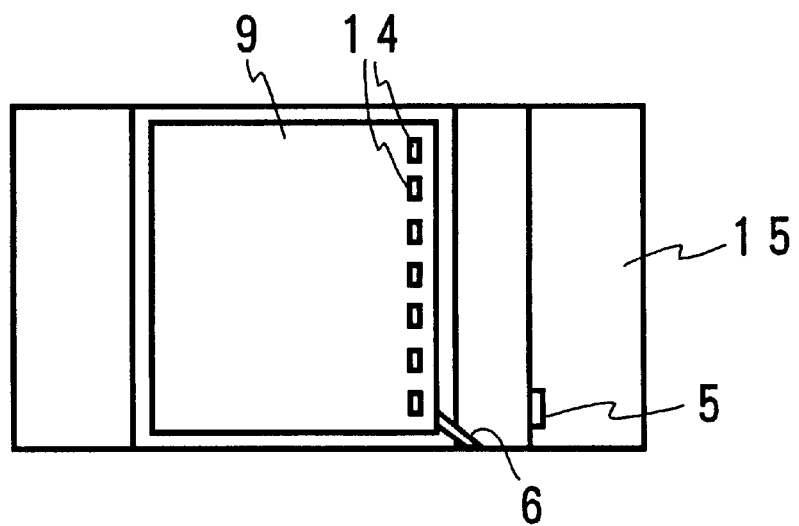

FIG. 3 shows another embodiment of the inventive electrophoresis apparatus, wherein a detachable power unit 15 is set on one end of the lid 2 covering the electrophoresis tank 1. The power unit 15 converts the alternating current supplied from the power source to a direct current, as well as has the fan 5 to send the outside air to the suction opening 4 perforated in the lid 2. As shown in FIG. 3, the lid 2 is not limited to have a structure showing the entire bottom of the electrophoresis tank 1, but may have a structure showing at least the flow of the sample in the agarose gel 9. According to this embodiment, a separate commercial A.C. power supply, a D.C. power supply or a fan is unnecessary, making the structure compact.

In the above-mentioned embodiments, a fan 5 is formed as a suction means on the suction opening 4 side of the lid 2. A fan may be formed as a discharge means on the exhaust opening 7 side thereof. Alternatively, the air supply direction from the fan 5 formed on the suction opening 4 side of the lid 2 may be reversed, so that the outside air is taken in from the exhaust opening 7 and discharged from the suction opening 4.

Figure 4:
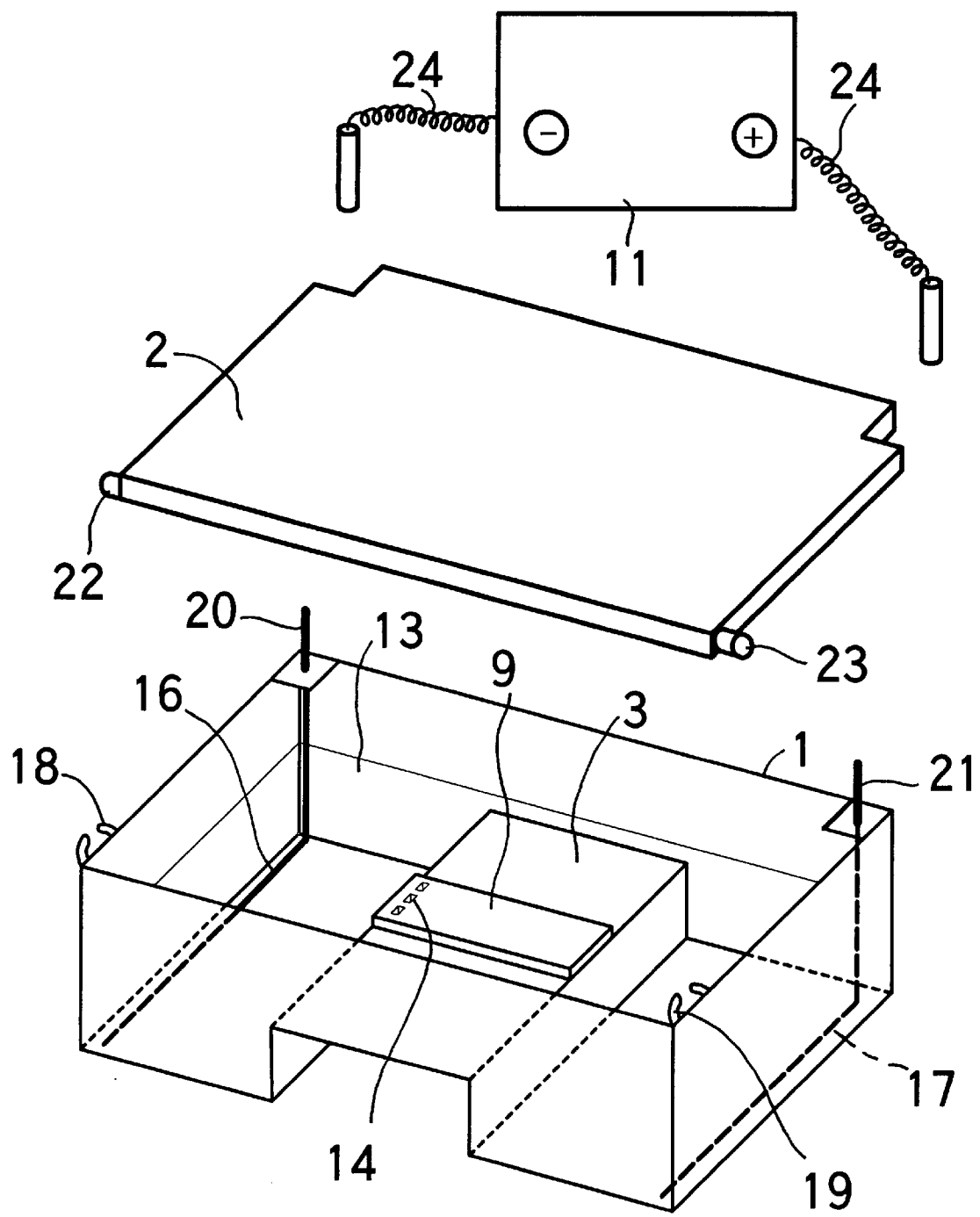
FIG. 4 is a perspective view showing one embodiment of the electrophoresis apparatus of the present invention.

FIG. 4 is a perspective view of another embodiment of the inventive electrophoresis apparatus, wherein a convex platform 3 is formed on the bottom of the electrophoresis tank 1 and cathode and anode 16 and 17 made from a platinum wire and the like are respectively formed on the both ends of the platform in the migration direction. Folk-shaped bearing parts 18 and 19 are respectively formed on the top of the sides at the both ends of the electrophoresis tank 1 in the migration direction and in the vicinity of one end of the sides in the direction forming a right angle with the migration direction. In the direction forming a right angle with the migration direction of the electrophoresis tank 1, both anode and cathode electrode terminals 20 and 21 protrude upward from the two corners opposite from the bearing parts 18 and 19, and the both electrode terminals 20 and 21 are connected to the cathode and anode 16 and 17, respectively.

The lid 2 to cover the electrophoresis tank 1 is made from transparent plastic, and has axes 22 and 23 extending toward the outside at the position corresponding to the bearing parts 18 and 19 of the electrophoresis tank 1. The axes 22 and 23 are elliptic columns having a minor axis extending in the direction of the thickness of the lid 2 and a major axis extending in the direction forming a right angle with the thickness direction of the lid 2. These shapes of the bearing parts 18 and 19 of the electrophoresis tank 1 and the axes 22 and 23 of the lid 2 allow free detachment and attachment of the lid 2, while keeping the thickness direction of the lid nearly horizontal and the direction orthogonal to the thickness direction of the lid 2 nearly vertical, by respectively fitting the axes 22 and 23 in the folk gaps in the bearing parts 18 and 19. By fitting the axes 22 and 23 in the bearing parts 18 and 19, respectively, a hinge is formed. Using this hinge as a fulcrum, the lid 2 can be shut with the migration direction as an axis.

For electrophoresis, an agarose gel 9 is placed on the platform 3 in the electrophoresis tank 1 filled with an electrophoresis buffer 13, while the lid 2 is retained open. The sample is placed in the slot 14 in the agarose gel 9, and after shutting the lid 2, the power cord 24 from the D.C. power supply 11 is connected to the anode and cathode electrode terminals 20 and 21, and a suitable voltage and suitable current are applied to establish conductivity. After the completion of the migration, the power cord 24 is removed; the lid 2 is opened to remove the gel 9.

Figure 5A:
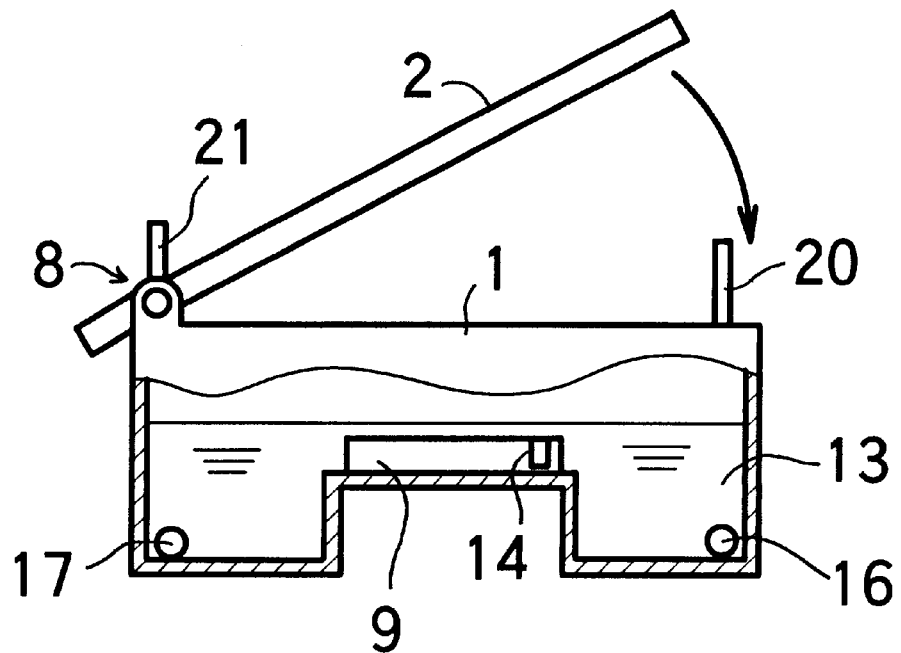
FIGS. 5(a), (b) show an embodiment wherein a lid 2 is fixed to the electrophoresis tank 1 by a hinge.
Figure 5B:
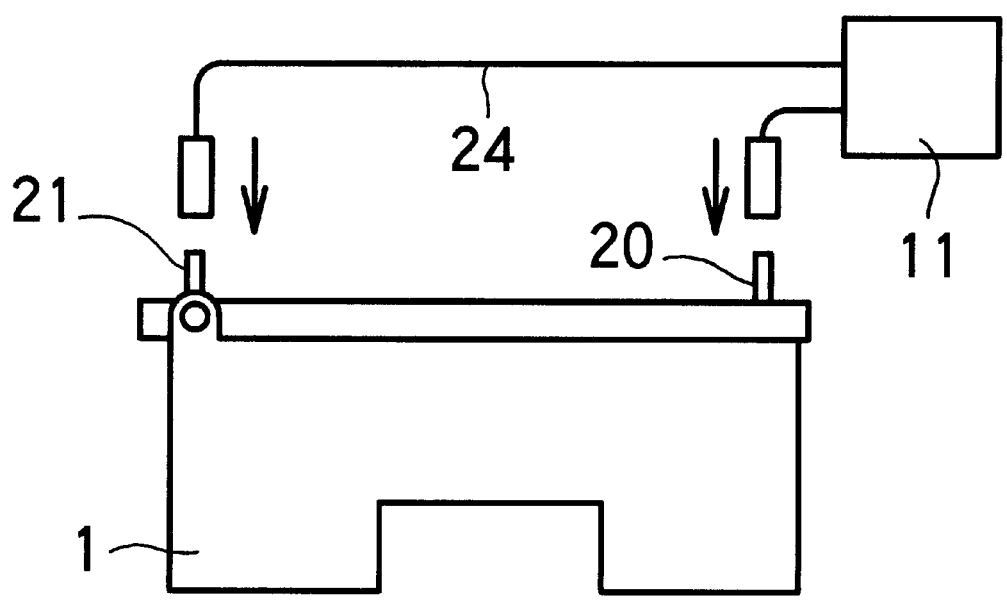

In the embodiment shown in FIG. 4, the lid 2 can be secured in a detachable manner to the electrophoresis tank 1. The lid 2 may be fixed to the electrophoresis tank 1 by the aid of a hinge. In FIG. 5, the lid 2 is fixed to the electrophoresis tank 1 by a hinge. In this embodiment, of the sides of the electrophoresis tank 1, the both sides extending in the migration direction, namely, a pair of sides on the cathode 16 side and the anode 17 side of the electrophoresis tank 1, are set to face each other. The hinge 8 is formed on the top end of the anode 17 side. Therefore, in the embodiment shown in Fig 5, the lid 2 can be shut with the direction forming a right angle with the migration direction as an axis.

During the migration, the water vapor generated from the electrophoresis buffer 13 is bedewed on the inner surface of the lid 2 (the plane opposite to the bottom of the electrophoresis tank 1), and when the lid 2 is opened, water droplets drip along the lid 2. In the embodiment of FIG. 5, since the anode 17 side end of the lid 2 protrudes outward from the side of the electrophoresis tank 1, when the lid 2 is opened, water droplets could drop outside the electrophoresis tank 1. To prevent such leakage, the structure of the lid 2 or the position of the hinge should be modified.

Figure 6:
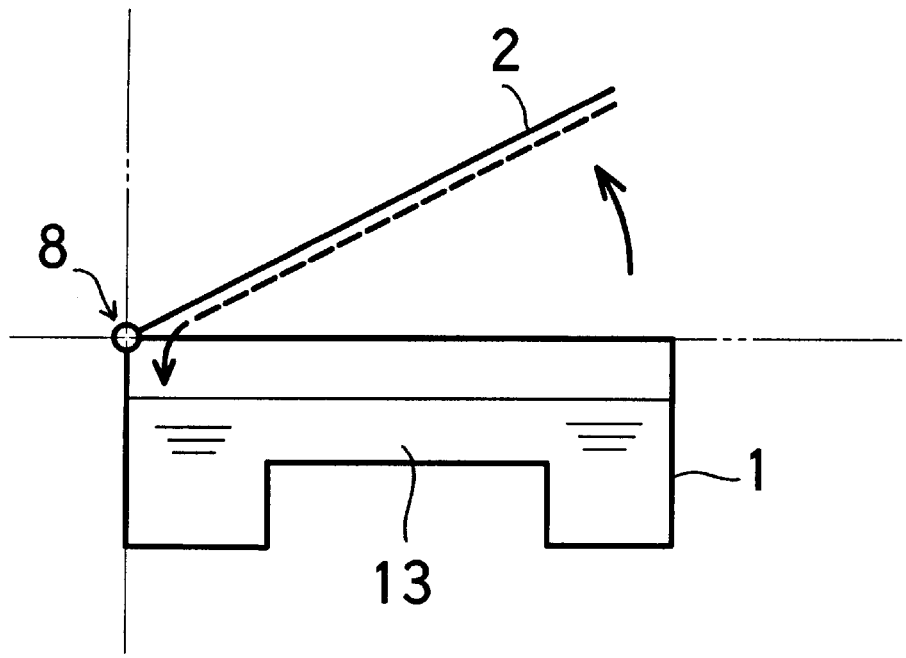
FIG. 6 shows an embodiment wherein water droplets are recovered into the electrophoresis tank 1.

FIG. 6 shows an embodiment to recover the water droplets in the electrophoresis tank 1, wherein the broken line shows the flow path of the water droplets. In this embodiment, a hinge 8 is set at the position where one side of the electrophoresis tank 1 meets the top end of the electrophoresis tank 1. Therefore, when the lid 2 is opened, water droplets drip along the lid 2 and flow into the electrophoresis tank 1 from the position of the hinge 8.

Figure 7:
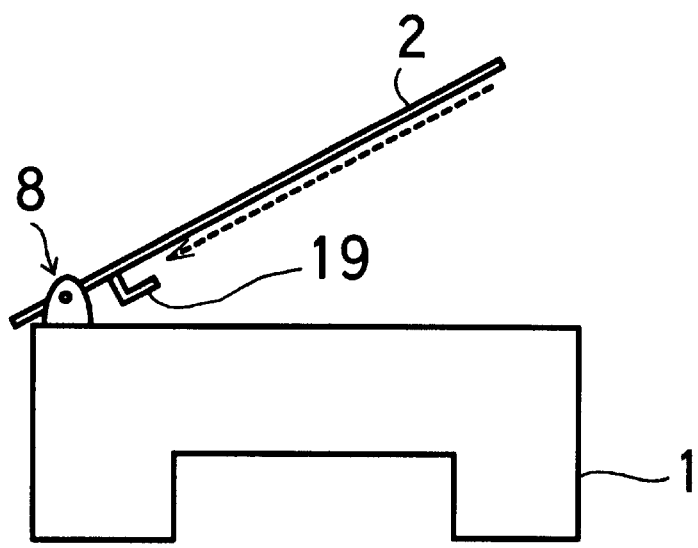
FIG. 7 shows an embodiment having a pool 25 inside the lid 2.

Besides the embodiment shown in FIG. 6, water droplets can be recovered within the electrophoresis tank 1 by forming a pool to recover water droplets or a water receiver on the lid 2 to receive water droplets and let them drip into the electrophoresis tank 1. In FIG. 7, a pool 19 is set on the lid 2, wherein the broken line shows the flow path of the water droplets. In the embodiment shown in FIG. 7, the position of the hinge 8 is not particularly limited. When the lid 2 is opened, water droplets drip along the lid 2 and are recovered in the pool 19.

Figure 8A:
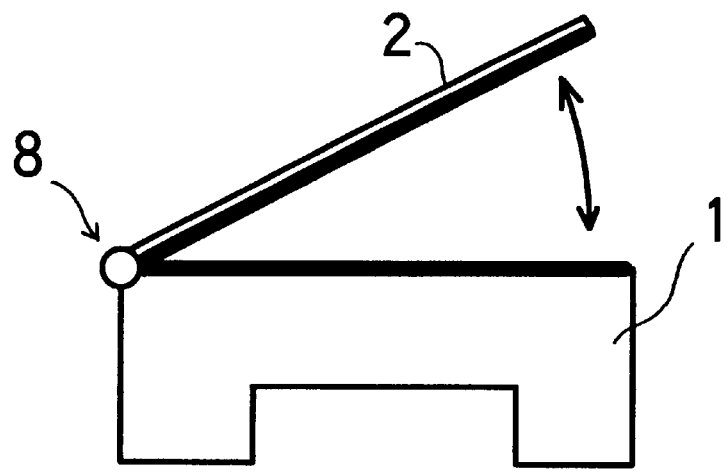
FIGS. 8(a)–(c) show an embodiment wherein the conductivity is controlled by opening or shutting the lid 2, wherein (a) shows the locations of the electrophoresis tank 1 and electrode terminal (thick line), (d shows a fit type electrode terminal, and (c) shows a contact type electrode terminal.
Figure 8B:
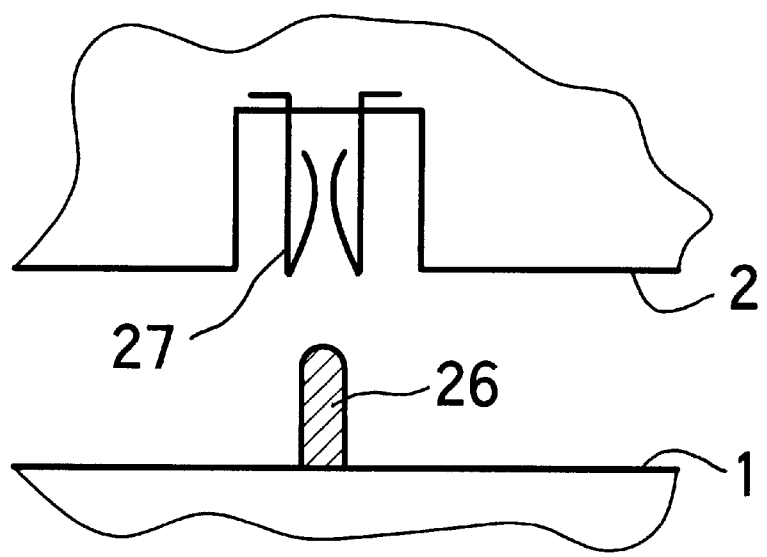
Figure 8C:
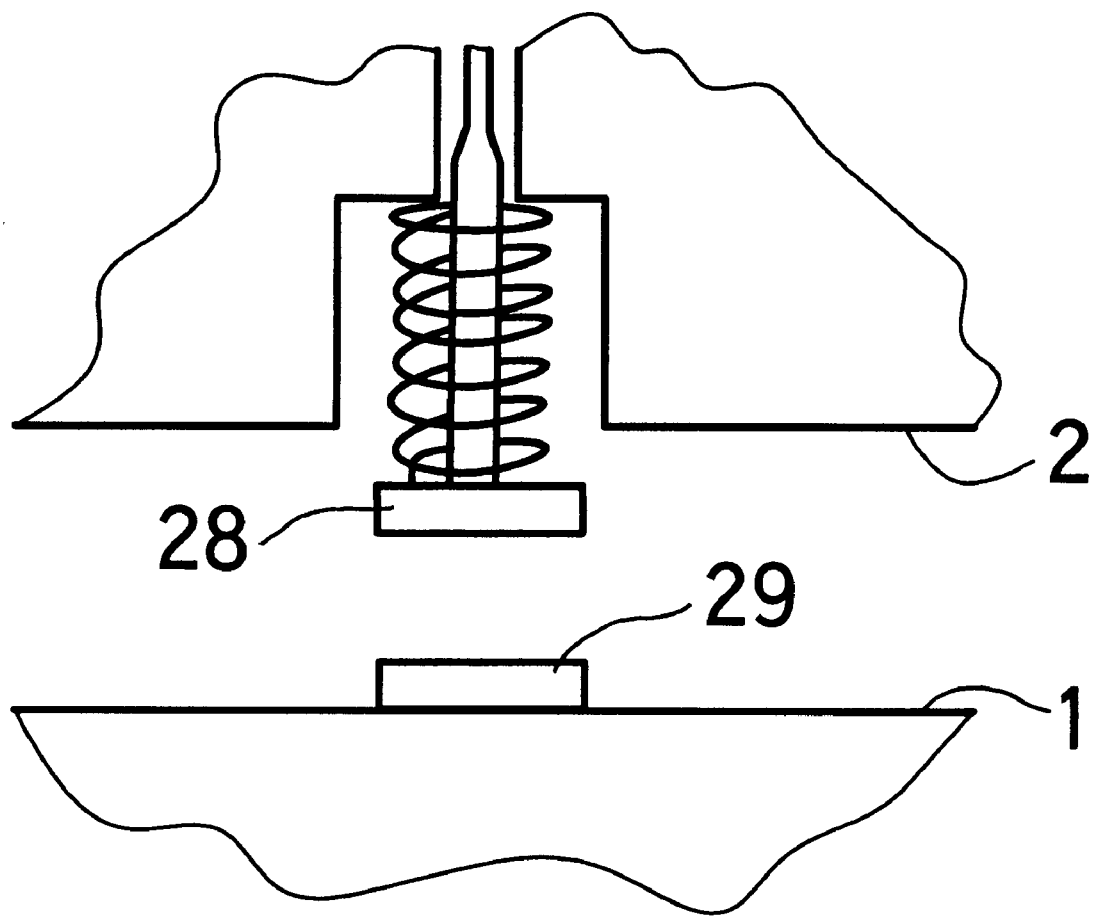

Another embodiment of the present invention is an electrophoresis apparatus wherein the conductivity is controlled by open and shut of the lid of the electrophoresis tank, which lid being fixed with a hinge. This embodiment is shown in FIG. 8. FIG. 8(a) schematically shows the lid 2 of the electrophoresis tank, which is fixed with a hinge, and the electrophoresis tank 1, wherein a terminal is set at some position where the electrophoresis tank 1 and the lid 2 come into contact with each other (shown with a thick line in the Figure). FIGS. 8(b) and 8(c) show typical electrode terminals.

FIG. 8(b) shows an embodiment where service terminals (male-female terminal) fit, in which, when the lid 2 is shut, a male pin 26 fits into a female receiver 27 (pin receiver) formed by a pair of plate springs, thus allowing contact of the both terminals to establish conductivity.

FIG. 8(c) shows a structure wherein the planar terminals come into contact, wherein one planar terminal 28 may be equipped with a spring as shown in this Figure or comprises a magnet that secures contact with the other planar terminal 29. These terminals in a pair are necessary for each of the cathode and anode. The shape of the terminal is not limited to these but may be any as long as the contact state can be secured.

Figure 9:
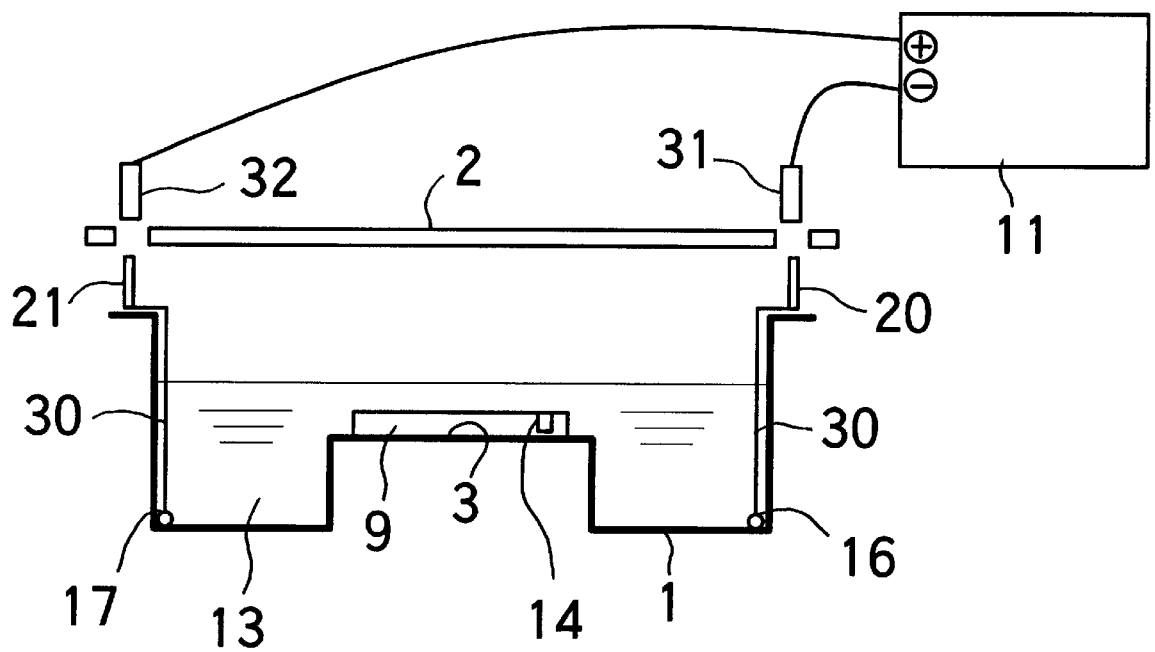
FIG. 9 is a schematic showing wherein the inventive electrophoresis apparatus is a horizontal submarine electrophoresis apparatus.

Another embodiment of the present invention is shown in FIG. 9. In FIG. 9, the electrophoresis tank 1 is a horizontal submarine electrophoresis tank; wherein the convex part formed in the near center of the bottom is a platform 3 on which an agarose gel 9 is placed. The agarose gel is prepared on a gel retention plate and the agarose gel carried on the gel retention plate is typically placed on the platform 3. The electrophoresis buffer 13 is filled in the electrophoresis tank 1 and agarose gel 9 is immersed therein. The cathode 16 and anode 17 made from a platinum wire are detachably formed near the both ends of the bottom of the electrophoresis tank 1 in the migration direction, and the both electrodes 16 and 17 are respectively connected to the cathode terminal 20 and anode terminal 21 formed on the electrophoresis tank 1, via a lead wire 30 which is covered with a heat resistant Teflon.

A transparent lid 2 to cover the opening of the electrophoresis tank 1 is set on the top thereof. The cathode and anode terminals 20 and 21 are connected to the cathode and anode power terminals 31 and 32 via the through-holes perforated in the lid 2, and a voltage is applied from the D.C. power supply 11. For electrophoresis, conductivity is established while a sample is placed in the slot 14 formed in the agarose gel 9 immersed in the buffer 13.

The cathode 16 and anode 17 in the electrophoresis tank 1 need to be set in a parallel relation to each other. As an easy means to secure a nearly parallel relation between the cathode 16 and anode 17, an electrode rack can be used. The electrode rack is equipped with an electrode connected to an electrode terminal, and is divided into a cathode rack carrying a cathode connected to a cathode terminal and an anode rack carrying an anode connected to an anode terminal. When an electrode rack is set within the electrophoresis tank, a plurality of slots extending to form an approximately right angle with the migration direction are set on the sides of the electrophoresis tank 1, respectively on the cathode side and anode side, and a part of the electrode rack is fit in a single slot on each electrode side for fixing same.

Figure 10:
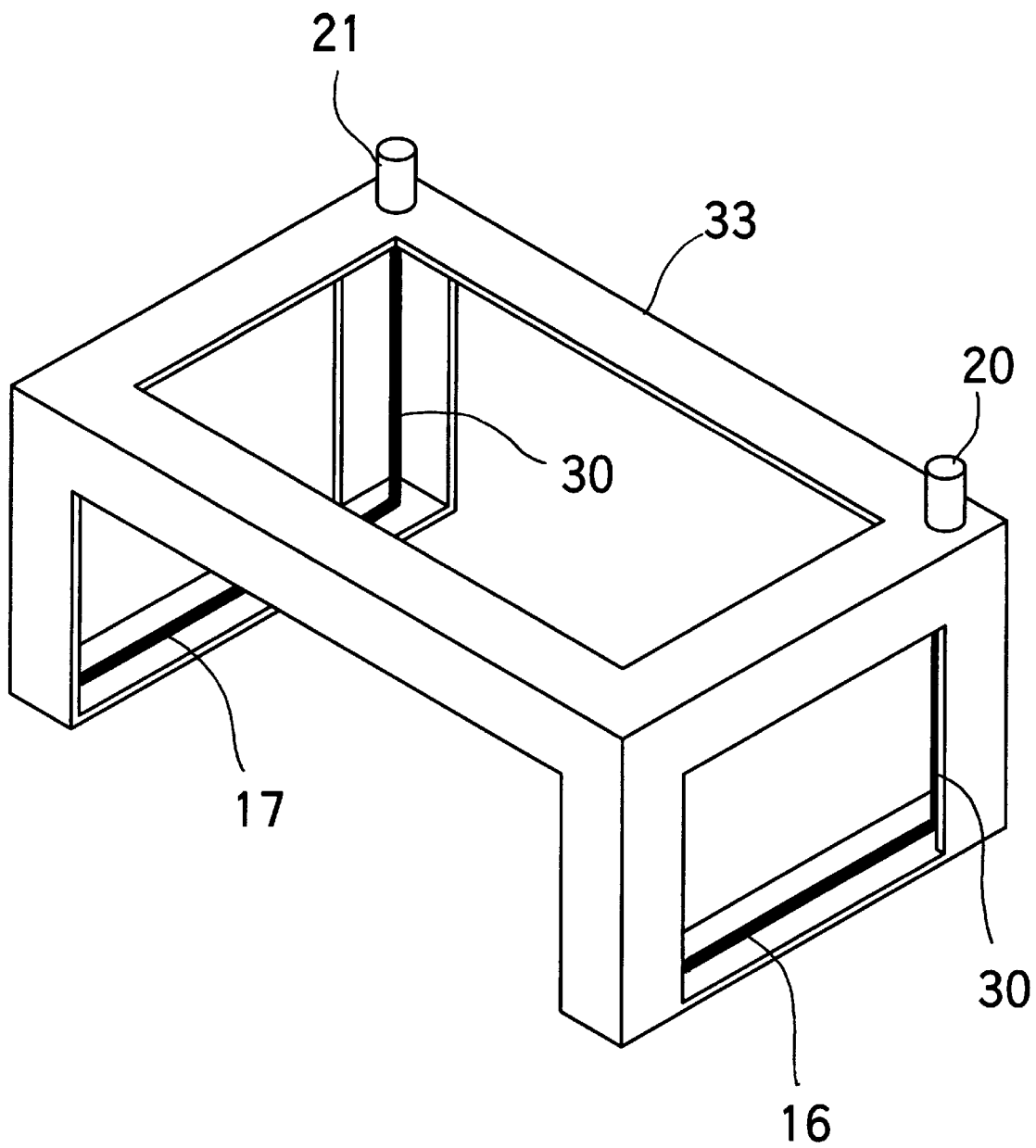
FIG. 10 is a perspective view of a detachable electrode rack 33.
Figure 11A:
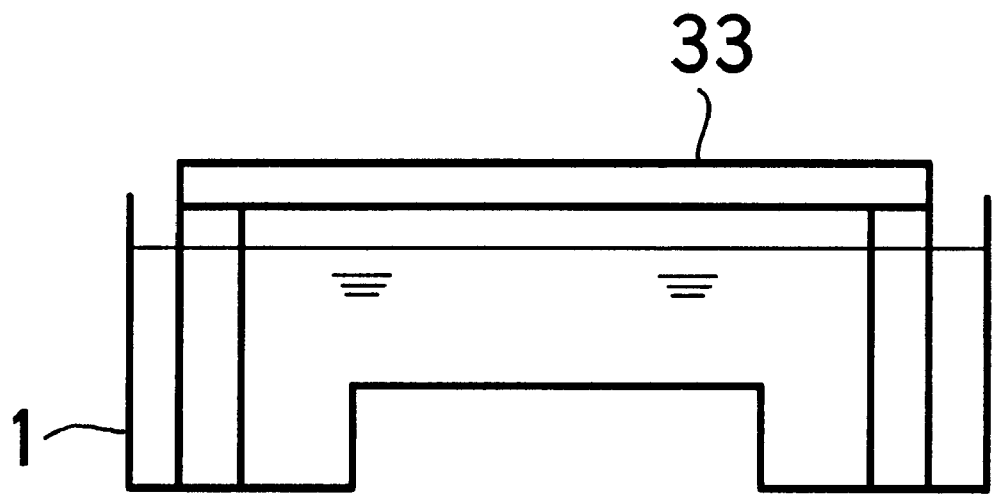
FIGS. 11(a), (b) show an embodiment of an electrophoresis apparatus wherein the distance between electrodes is changeable.
Figure 11B:
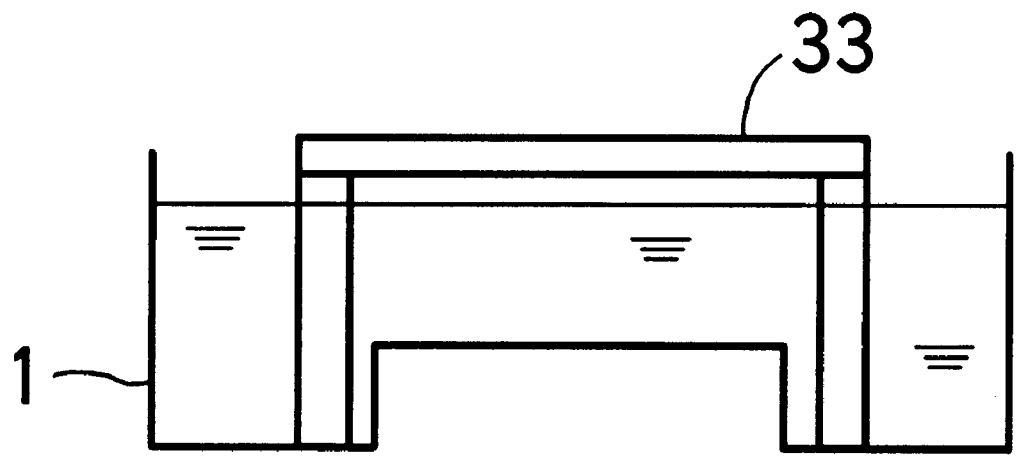

As shown in FIG. 10, a member wherein an anode rack and a cathode rack are integrally formed may be used. In the electrode rack 33 shown in FIG. 10, columns hang from the corners of the rectangular frame, so that the mutually parallel cathode 16 and anode 17 are formed to connect the two columns beneath the short sides of the frame. At the both ends of the long side of the frame protrude the cathode terminal 20 and anode terminal 21 in the upward direction. The both terminals 20 and 21 are respectively connected to the cathode 16 and anode 17 via the lead wire 30. In the embodiment shown in FIG. 10, the length of the long side of the electrode rack 33 is almost identical with the distance between the cathode 16 and anode 17. Thus, when two kinds of electrode racks 33 having a smaller length of the long side [FIG. 11(b)] and electrode rack 33 having a greater length of the long side [FIG. 11(a)] are used as shown in FIG. 11, a single large electrophoresis tank 1 can also function as an electrophoresis apparatus for electrophoresis using a minigel.

Figure 12:
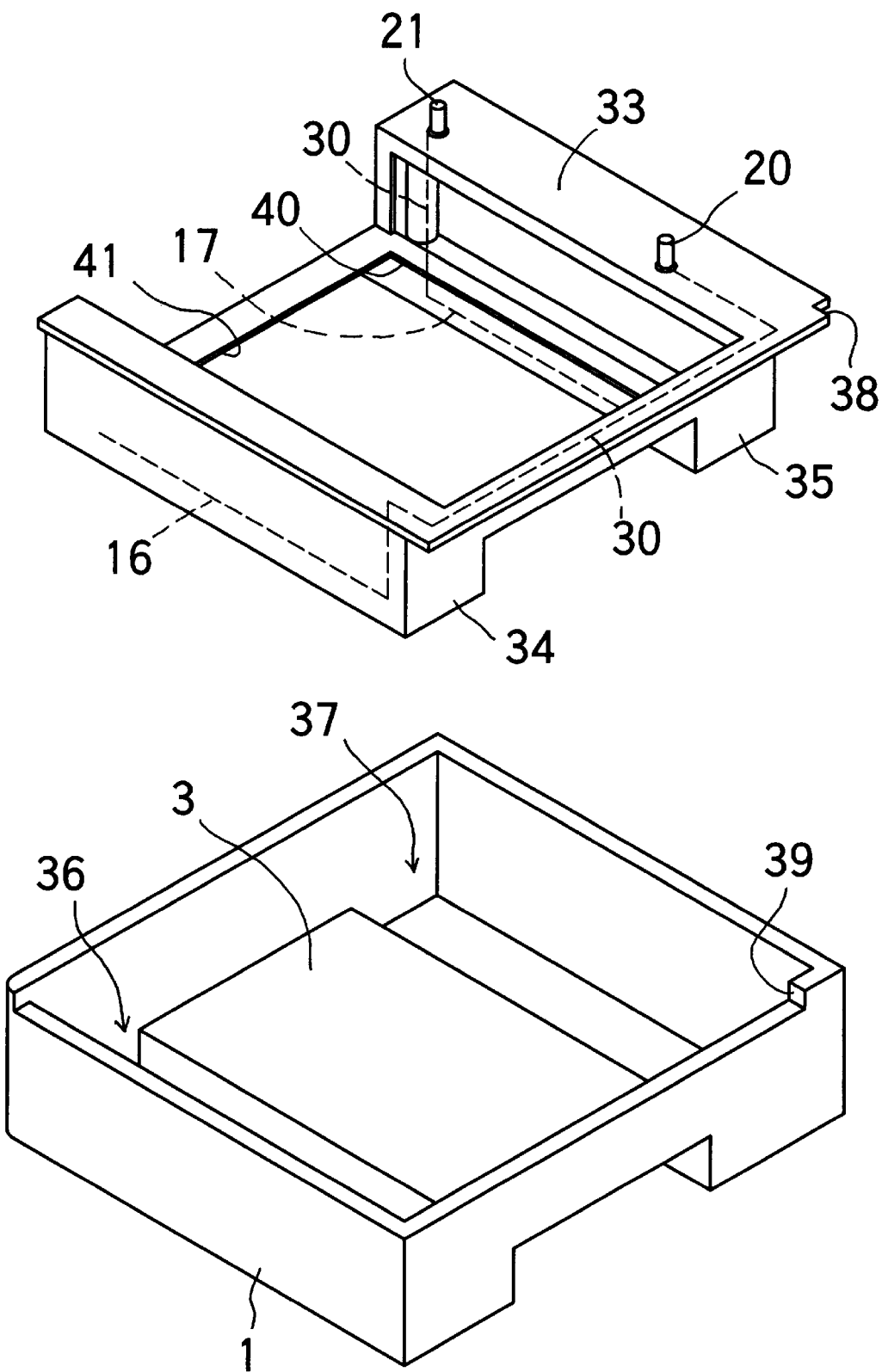
FIG. 12 is a perspective view of another embodiment of an electrophoresis apparatus wherein an anode rack and a cathode rack are integrated.

FIG. 12 shows another embodiment wherein an anode rack and a cathode rack are integrated The electrode rack 33 shown in FIG. 12 is formed by connecting the cathode side leg part 34 to which cathode 16 is fixed, and the anode side leg part 35 to which cathode 17 is fixed. In the electrode rack 33 shown in FIG. 12, the cathode terminal 20 and the anode terminal 21 protrude upward from the top thereof, and are respectively connected to the cathode 16 and anode 17 fixed nearly in parallel relation to each other at the downside, via the lead wire 30.

The electrode rack 33 is fixed to the electrophoresis tank 1 with its cathode side leg part 34 and anode side leg part 35 respectively fixed in the cathode side trench 36 and anode side trench 37 inside the electrophoresis tank 1, and the broken-away part 38 on the electrode rack 33 secured at the secure part 39 of the electrophoresis tank 1. In this manner, the periphery 40 of the beam of the electrode rack 33 and the periphery 41 of the connecting beam abut against the periphery of the gel retention plate placed on the platform 3 in the electrophoresis tank 1 to prevent sliding of the gel retention plate. According to this embodiment, a part of the electrode rack 33 (e.g., cathode side leg part 34 and anode side leg part 35) fits in the electrophoresis tank 1, so that the amount of the electrophoresis buffer 13 to be filled in the electrophoresis tank 1 can be reduced. Moreover, since the electrode rack 33 consists of board-like members connected to each other, it has an ideal shape which stands deformation upon autoclaving when a heat resistant material is used to form the board-like members.

Figure 13:
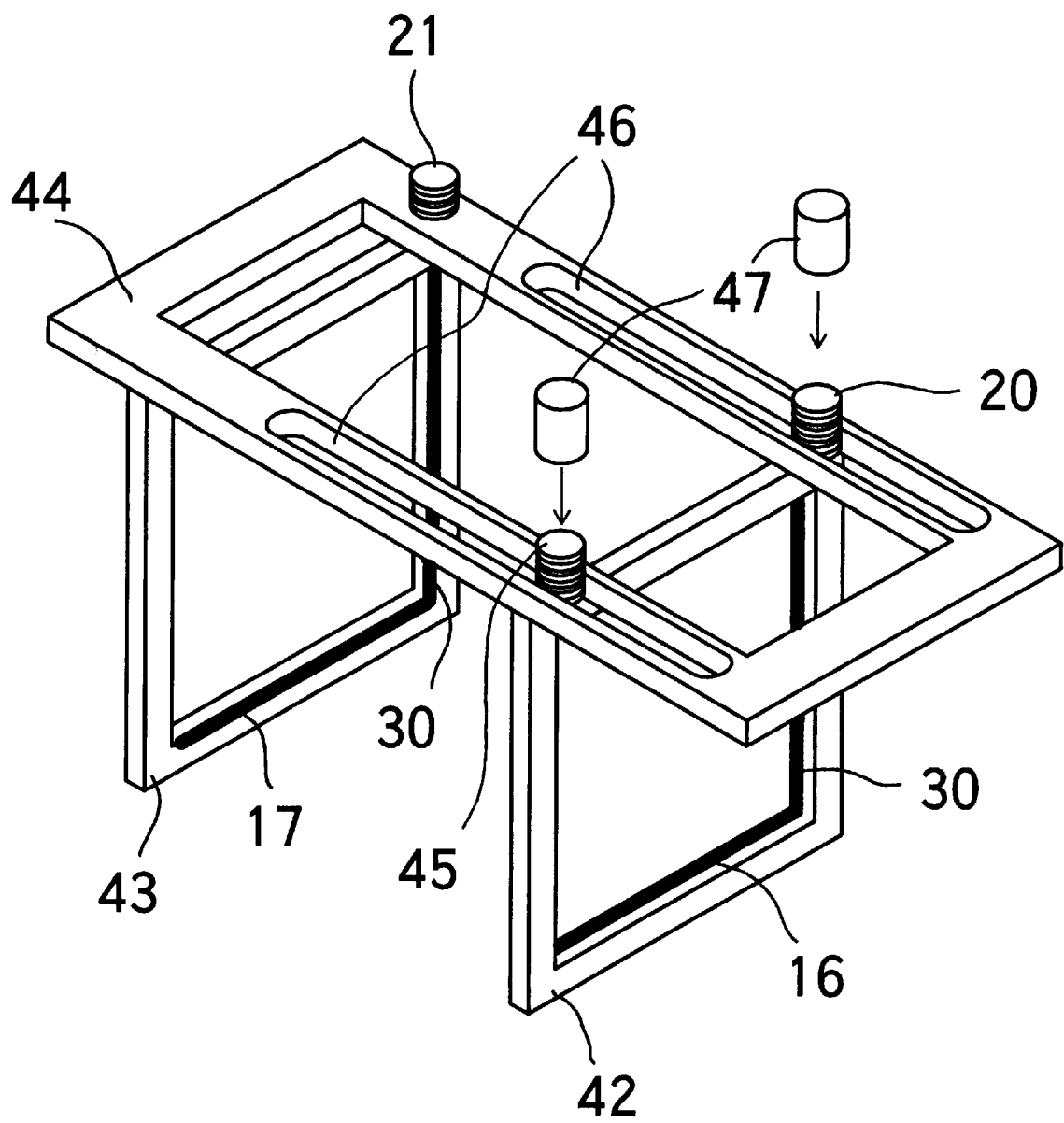
FIG. 13 is a perspective view of one embodiment wherein the distance between the cathode and anode can be changed.

FIG. 13 shows an embodiment wherein the distance between the anode and cathode electrodes can be changed by a single member. The cathode rack 42 carrying a cathode 16 and an anode rack 43 carrying an anode 17 are supported by an electrode support 44, which is a rectangular frame, in such a manner that they become mutually parallel to each other. The anode rack 43 has an anode terminal 21 connected to the anode 17 via the lead wire 30, and is fixed by the lower surface of the electrode support 44. The anode terminal 21 passes through the through-hole perforated in one long strip of the electrode support 44 and protrudes upward.

On the other hand, a cathode terminal 20 connected to the cathode 16 via the lead wire 30 is formed on the cathode rack 42, and an external thread 45 is formed on the same side with this cathode terminal 20. A through-hole 46 extending in the longitudinal direction is formed on the both long strips of the electrode support 44. The cathode terminal 20 of the cathode rack 42 and external thread 45 respectively protrude upward passing the through-hole 46. In this embodiment, the cathode terminal 20 has a function of an external thread. It displaces the cathode rack 42 in the longitudinal direction and, while retaining the cathode 16 and anode 17 nearly parallel, fixes the cathode rack 42 to the electrode support 44 with the internal thread 47.

The embodiment wherein a single member changes the distance between the cathode and anode is not limited to the one shown in FIG. 13. For example, in FIG. 13, a rail-like convex part extending in the longitudinal direction may be formed on the plane (lower plane) against which the cathode rack 42 beneath the electrode support 44 abuts, and a concave part capable of fitting in this convex part and of dislocation in the longitudinal direction may be formed on the cathode rack 42, whereby the cathode rack 42 is fixed at a certain distance between the electrodes.

Figure 14:
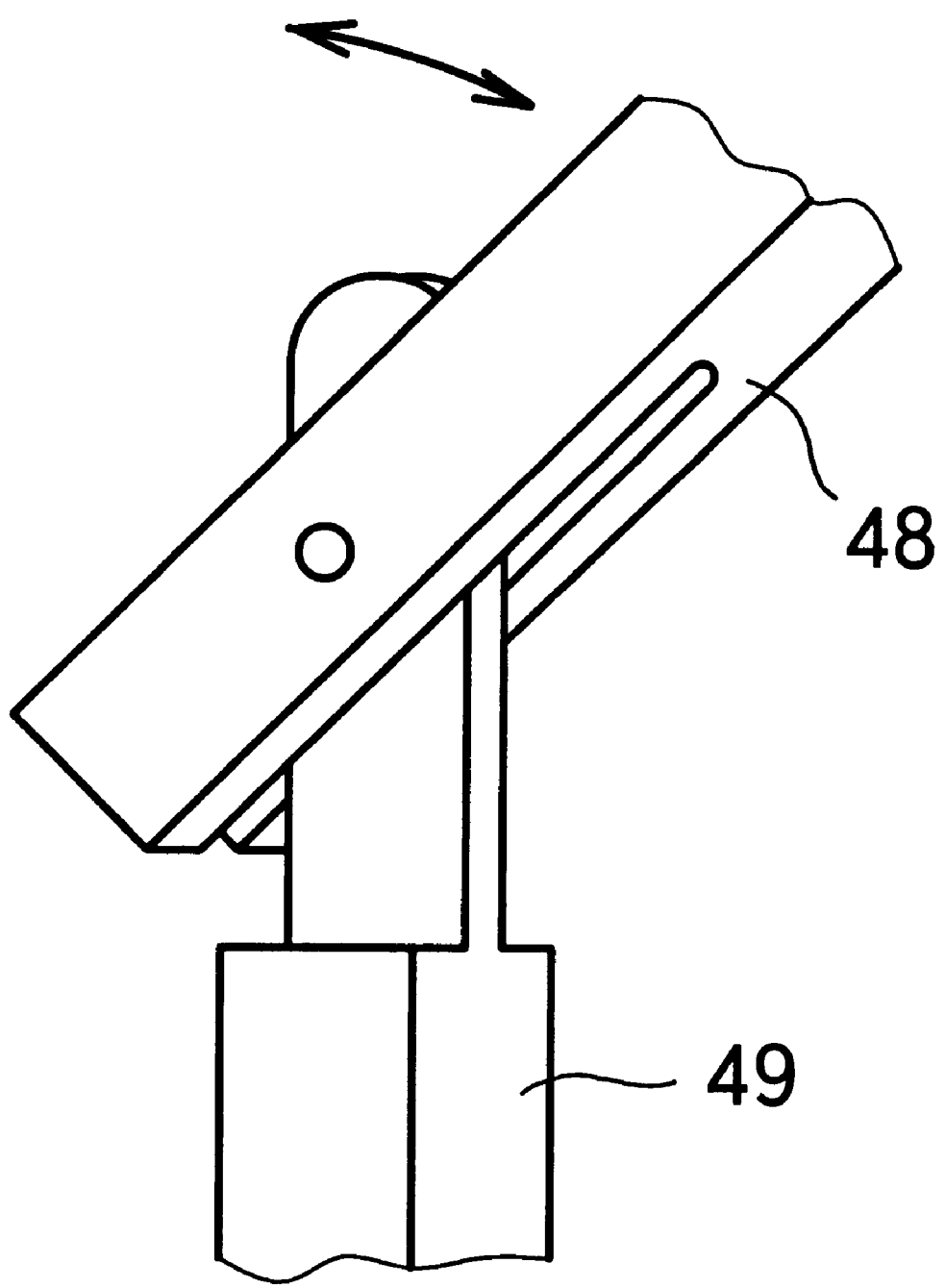
FIG. 14 is a partial perspective view of one embodiment wherein the leg part of an electrode rack is folded at the near center thereof.
Figure 15A:
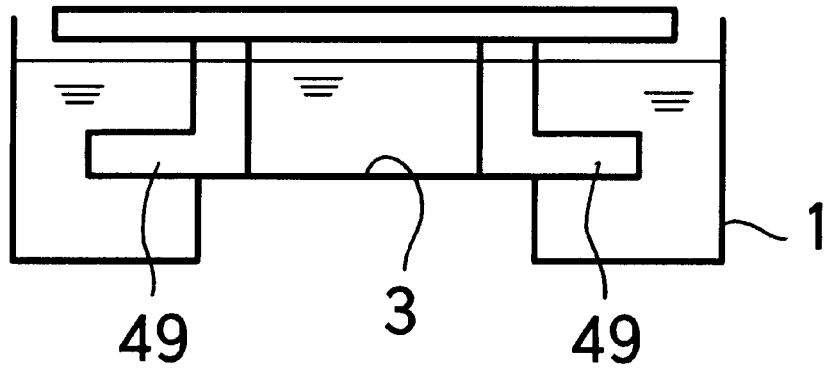
FIGS. 15(a)–(c) show electrophoresis structures wherein the depth can be controlled.
Figure 15B:
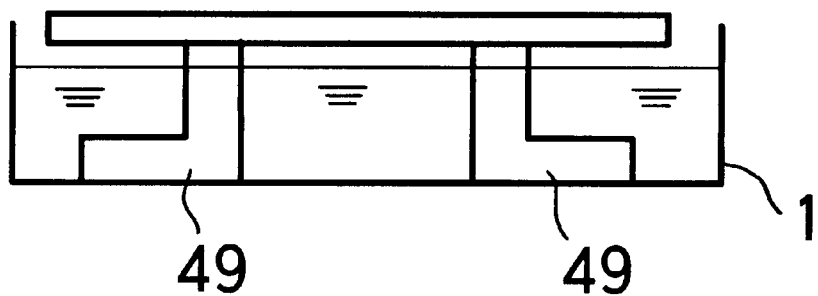
Figure 15C:
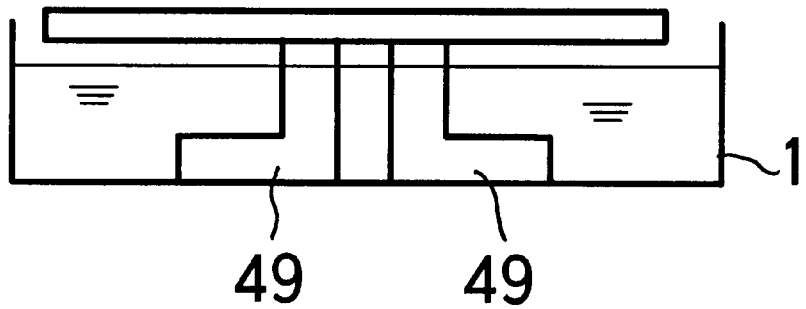

FIG. 14 is a partial perspective view showing an embodiment wherein the leg part of the electrode rack is folded in the near center thereof. A hinge binds the upper part 48 and the lower part 49 of the leg part, and where necessary, the leg part can be folded. This enables control of the depth, and as shown in FIG. 15(a), it can be used in any horizontal submarine electrophoresis tank 1. As shown in FIG. 15(b) and 15(c), it can be used in an electrophoresis tank 1 without a gel platform 3, such as a rectangular solid bath. It is rather preferable to use a box without the platform 3 as the electrophoresis tank 1, because the bottom of the electrophoresis tank 1 becomes flat and does not limit the distance between the electrodes.

The electrophoresis apparatus of the present invention may be a combination of the characteristics optionally selected from those described above. For example, an electrophoresis apparatus comprising an electrophoresis tank and a transparent or semi-transparent lid, combined with the following characteristics may be exemplified.

a. A means for forcibly discharging the air in the space between the electrophoresis tank and the lid to the outside or a means for forcibly absorbing the outside air into said space.

b. An air suction opening in the periphery of the lid, and an air exhaust opening in the periphery facing said suction opening.

c. A lid capable of being opened and shut by the action of a hinge having a fulcrum on one side or a pair of opposing sides of the electrophoresis tank.

d. Electrode racks respectively carrying a cathode connected to a cathode terminal and an anode connected to an anode terminal, which are detachably set in the electrophoresis tank.

e. A contact between the electrode terminal and the power supply to apply a D.C. voltage to the electrode, which is controlled by the open and shut of the lid.

Besides the above, a suction means may be attached to the outside of the suction opening.

In addition, an arched lid having the top thereof at one end thereof in the migration direction and having growing gradients toward the other end thereof in the migration direction may be used.

Furthermore, a baffle plate may be attached to the inner surface of the lid, which baffle forming an angle with the migration direction.

The present invention is explained in more detail by way of Examples, to which the present invention is not limited.

EXAMPLE 1

Using an apparatus shown in FIG. 3, whether or not the clouding and bedewing due to the vapor generated from the buffer during electrophoresis is removed effectively by constantly sending the air to the inner surface of the lid of the electrophoresis tank, was tested.

The buffer used was a widely used Tris-acetate buffer or Tris-borate buffer. Without placing a gel, a 7 V/cm constant voltage was applied to establish conductivity without activating a fan. All buffers were applied from room temperature. In about 5 min, fine water droplets attached to the inner surface of the lid, making the observation of the inside difficult. In about 10 min, the inside could not be observed at all and the water droplets began to gather. In about 20 min, water droplets started dripping. The temperature of the Tris-acetate buffer increased about 5 degrees in 30 min and in the case of the Tris-borate buffer, the temperature rise was about 3 degrees. After 5 min from the establishment of conductivity, the observation of the inside became completely unattainable.

Then, the conductivity was established under the same conditions while activating the fan of the apparatus. By 90-min energizing, the temperature of the buffer increased 12 degrees from the room temperature (22° C.) for the Tris-acetate buffer, and 8 degrees for the Tris-borate buffer, but the lid did not become cloudy. By the subsequent 90-min energizing, the lid did not become cloudy. In the case of the This-acetate buffer, the temperature increased 21 degrees from the room temperature, and 15 degrees for the This-borate buffer. By the subsequent 90-min energizing, the lid did not become cloudy. In the case of the Tris-acetate buffer, the temperature increased 28 degrees from the room temperature, and 19 degrees for the Tris-borate buffer.

For the recurrence of the conditions similar to the actual conditions, 0.8%, 1.0% and 1.2% agarose gels were placed in apparatuses and similar testing was conducted. The obtained results were similar to those obtained above.

EXAMPLE 2

Recovery of bedewed water on the inner surface of the lid of the electrophoresis tank-(I).

A hinge was formed in the electrophoresis tank, the lid was fixed and the apparatus shown in FIG. 6 was fabricated to study the path of the bedewed water after electrophoresis. The time necessary for producing bedewed water varies depending on the size of the electrophoresis tank and voltage. Generally, 1 hr was enough to produce bedewed water of a dripping degree on the inner surface of the lid. The bedewed water moved toward the hinge side of the lid as the lid was opened, gathered and dropped in the electrophoresis tank. Thus, the bedewed water could be effectively recovered in the electrophoresis tank.

EXAMPLE 3

Recovery of bedewed water on the inner surface of the lid of the electrophoresis tank-(II).

A hinge was formed on the electrophoresis tank, the lid was fixed and the apparatus shown in FIG. 7 was fabricated to study the path of the bedewed water after electrophoresis. The time necessary for producing bedewed water varies depending on the size of the electrophoresis tank and voltage. Generally, 1 hr was enough to produce bedewed water of a dripping degree on the inner surface of the lid. The bedewed water moved toward the hinge side of the lid as the lid was opened, gathered and moved into the pool. Thus, the bedewed water could be effectively recovered in the pool formed on the inner surface of the lid.

EXAMPLE 4

Power switch according to open and shut of the lid.

The apparatus shown in FIG. 8 was fabricated and the action of the power switch according to the open and shut of the lid was studied. Both fit type and contact type switches responded to the slight difference in the angles formed by the open and shut of the lid and sufficiently functioned as a switch.

EXAMPLE 5

Using the electrode support shown in FIG. 13, the distance between the electrodes was varied and electrophoresis was carried out. When the distance between the electrodes was 12 cm, the application of 100 V voltage resulted in practical function as an apparatus for a minigel. The migration time was about 30 min. When the distance between the electrodes was the maximum distance of the electrophoresis tank, i.e., 24 cm and 30 cm tried, the application of 100 V voltage resulted in the same degree of resolution as that obtained by conventional electrophoresis tank.

According to the electrophoresis apparatus of the present invention, the air always flows in a constant direction along the lid, thereby efficiently capturing and discharging the water vapor inevitably generated by the electrophoresis. Consequently, the inside of the lid does not become cloudy or have news, and the inside of the electrophoresis tank can be easily observed during electrophoresis. Thus, safe and ensured electrophoresis can be carried out.

According to the electrophoresis apparatus of another embodiment of the present invention, moreover, operability can be enhanced. In addition, bedewed water occurred during the electrophoresis can be prevented from being leaked outside the electrophoresis tank. This ultimately minimizes the surrounding area that becomes wet. Further, an extra space is not necessary on the test table, and by utilizing the open and shut action of the lid, a safety device of the power supply can be easily attained.

According to the electrophoresis apparatus of another embodiment of the present invention, the distance between two electrodes can be freely controlled, which in turn makes it possible to control resolution and migration speed by the application of the same voltage, and to use conventional electrophoresis tanks for electrophoresis using a minigel. Inasmuch as the separation of both electrodes or both electrode racks from the electrophoresis tank is possible, the whole electrophoresis tank after use can be washed with ease, thereby eliminating the risk of erroneously damaging the electrodes. Moreover, attachment of the electrodes is facilitated to improve production efficiency.

Other embodiments are also encompassed in the scope of the appended claims.

This application is based on application Nos. 93997/1997, 96195/1997 and 100171/1997 filed in Japan, the contents of which are incorporated hereinto by reference.

What is claimed is:

1. A horizontal submarine electrophoresis apparatus comprising a horizontal submarine electrophoresis tank and a transparent or semi-transparent lid, said apparatus comprising a means for forcibly discharging the air in the space between said electrophoresis tank and said lid to the outside or a means for forcibly absorbing the outside air into said space, an air suction opening and an exhaust opening.

2. The electrophoresis apparatus of claim 1, wherein the air suction opening is formed in the periphery of the lid and the air exhaust opening is formed in the periphery facing said suction opening.

3. The electrophoresis apparatus of claim 1, wherein the discharge means or the suction means is formed on the lid.

4. The electrophoresis apparatus of claim 1, wherein the lid is arched, has a top thereof at one end thereof in the migration direction of the electrophoresis tank, and has growing gradients toward the other end thereof in the migration direction.

5. The electrophoresis apparatus of claim 1, wherein the lid includes a top surface which slides down from the top part on one end of the lid in a migration direction toward the other end of the lid in the migration direction, and a side on one end in the migration direction has the suction opening perforated in the upper part and toward a corner from the center.

6. The electrophoresis apparatus of claim 5, wherein the suction means is formed outside the suction opening.

7. The electrophoresis apparatus of claim 6, further comprising a baffle plate set inside the suction opening in the lid, forming an angle with the migration direction.

8. The electrophoresis apparatus of claim 1, wherein the lid is opened and shut by a hinge having a fulcrum on one side or on a pair of opposing sides of the electrophoresis tank.

9. The electrophoresis apparatus of claim 8, wherein the opening of the electrophoresis tank is square, and the outer periphery of the lid corresponds to the opening of the electrophoresis tank, said lid having a top surface sliding down from the center axis used when the lid is opened with the aid of a hinge, toward the opposite end of the lid, and the sliding surface being arched with growing gradients toward the downward direction of the lid.

10. The electrophoresis apparatus of claim 8, wherein the discharge means or the suction means is set on the lid.

11. The electrophoresis apparatus of claim 8, wherein the contact between an electrode terminal connected to an electrode set in the electrophoresis tank and power supply to apply a D.C. voltage to the electrode is controlled by opening and shutting the lid.

12. The electrophoresis apparatus of claim 1, further comprising a water receiver to let water droplets drip into the electrophoresis tank or a pool set on the inner surface of the lid to recover water droplets.

13. The electrophoresis apparatus of claim 1, wherein the contact between an electrode terminal connected to an electrode set in the electrophoresis tank and a power supply to apply a D.C. voltage to the electrode is controlled by opening and shutting the lid.

14. The electrophoresis apparatus of claim 1, wherein cathode and anode electrodes are detachably set in the electrophoresis tank.

15. The electrophoresis apparatus of claim 1, further comprising electrode racks, respectively carrying a cathode electrode connected to a cathode terminal and an anode electrode connected to an anode terminal, which are detachably set in the electrophoresis tank.

16. An electrophoresis apparatus comprising an electrophoresis tank and a transparent or semi-transparent lid, which is characterized by comprising the following (a) to (e):

(a) a means for forcible discharging the air in a space between an electrophoresis tank and a lid to the outside or a means for forcibly absorbing the outside air into said space, (b) an air suction opening in the periphery of the lid, and an air exhaust opening in the periphery facing said suction opening, (c) a lid capable of being opened and shut by the action of a hinge having a fulcrum on one side or a pair of opposing sides of the electrophoresis tank, (d) electrode racks respectively carrying a cathode connected to a cathode terminal and an anode connected to an anode terminal, which are detachably set in the electrophoresis tank, and (e) a contact between the electrode terminal and a power supply to apply a D.C. voltage to the electrode, which is controlled by opening and shutting the lid.

17. The electrophoresis apparatus of claim 16, wherein the suction means is attached outside the suction opening.

18. The electrophoresis apparatus of claim 17, comprising an arched lid having a top thereof at one end thereof in the migration direction of the electrophoresis tank and growing gradients toward the other end thereof in the migration direction.

19. The electrophoresis apparatus of claim 18, comprising a baffle plate inside the suction opening in the lid, forming an angle with the migration direction.

* * * * *